United States Patent
Couture

(10) Patent No.: US 11,389,145 B2
(45) Date of Patent: Jul. 19, 2022

(54) MAGNETORHEOLOGICAL FORCE RETRACTOR

(71) Applicant: Orthosoft ULC, Montreal (CA)

(72) Inventor: Pierre Couture, Montreal (CA)

(73) Assignee: Orthosoft ULC, Montral (CA)

( * ) Notice: Subject to any disclaimer, the term of this patent is extended or adjusted under 35 U.S.C. 154(b) by 373 days.

(21) Appl. No.: 16/717,342

(22) Filed: Dec. 17, 2019

(65) Prior Publication Data

US 2020/0187928 A1    Jun. 18, 2020

Related U.S. Application Data

(60) Provisional application No. 62/780,731, filed on Dec. 17, 2018.

(51) Int. Cl.
    *A61B 17/02*    (2006.01)
    *A61B 34/30*    (2016.01)
    *A61B 17/08*    (2006.01)
    *A61B 34/20*    (2016.01)
    (Continued)

(52) U.S. Cl.
    CPC .......... *A61B 17/02* (2013.01); *A61B 17/0206* (2013.01); *A61B 17/08* (2013.01); *A61B 34/20* (2016.02); *A61B 34/30* (2016.02); *A61B 34/32* (2016.02); *A61B 2017/00398* (2013.01);
    (Continued)

(58) Field of Classification Search
    CPC ...... A61B 17/0206; A61B 17/02; A61B 34/30
    See application file for complete search history.

(56) References Cited

U.S. PATENT DOCUMENTS

| 2001/0020121 A1* | 9/2001 | Hu ..................... A61B 90/57 600/210 |
| 2001/0025905 A1* | 10/2001 | Carpenter .............. A61B 90/50 248/231.71 |

(Continued)

FOREIGN PATENT DOCUMENTS

| WO | WO-2016160272 A1 * | 10/2016 | ............. A61B 90/50 |
| WO | WO-2016160272 A1 | 10/2016 | |

OTHER PUBLICATIONS

"Canadian Application Serial No. 3,065,443, Office Action dated Feb. 17, 2021", 3 pgs.

(Continued)

*Primary Examiner* — Christian A Sevilla
(74) *Attorney, Agent, or Firm* — Schwegman Lundberg & Woessner, P.A.

(57) ABSTRACT

The present disclosure can include a system including a surgical arm, a retractor connected to the surgical arm, a force sensor mounted on the surgical arm, the force sensor configured to receive sensor data indicating force on the retractor from the force sensor, and a magnetorheological fluid actuator for actuating the surgical arm, the actuator configured to actuate according to the received sensor data, and adjust the surgical arm according to the received sensor data so as to maintain a constant retraction force. The present disclosure can additionally include a method for retracting tissue including applying force to the tissue with a magnetorheological fluid actuator to induce a retraction force, sensing a change in force applied to the tissue using a force sensor, and maintaining the retraction force by adjusting the force applied to the tissue.

8 Claims, 7 Drawing Sheets

(51) Int. Cl.
*A61B 34/32* (2016.01)
*A61B 17/00* (2006.01)

(52) U.S. Cl.
CPC ............... *A61B 2017/00473* (2013.01); *A61B 2017/00477* (2013.01)

(56) References Cited

U.S. PATENT DOCUMENTS

| | | |
|---|---|---|
| 2002/0026101 A1* | 2/2002 | Bookwaiter ....... A61B 17/0293 600/231 |
| 2002/0113424 A1* | 8/2002 | Smith, Jr. .......... B60R 22/3413 280/806 |
| 2004/0186356 A1 | 9/2004 | Omalley et al. |
| 2012/0130180 A1 | 5/2012 | Pell et al. |
| 2018/0132839 A1* | 5/2018 | Friedrich ............... A61B 34/76 |
| 2018/0153585 A1* | 6/2018 | Levine ............... A61B 17/1655 |

OTHER PUBLICATIONS

"Canadian Application Serial No. 3,065,443, Office Action dated Oct. 26, 2021", 4 pgs.
"Canadian Application Serial No. 3,065,443, Response filed Feb. 23, 2022 to Office Action dated Oct. 26, 2021", 10 pgs.
"Canadian Application Serial No. 3,065,443, Response filed Jun. 17, 2021 to Office Action dated Feb. 17, 2021", 9 pgs.

\* cited by examiner

MAGNETORHEOLOGICAL FORCE RETRACTOR

CROSS-REFERENCE TO RELATED APPLICATIONS

This application claims the benefit of priority to U.S. Provisional Patent Application Ser. No. 62/780,731 entitled "MAGNETORHEOLOGICAL FORCE RETRACTOR," filed Dec. 17, 2018, the disclosure of which is incorporated herein in its entirety by reference.

BACKGROUND

The present invention relates generally to apparatus and systems for supporting surgical procedures and tools. Some surgical procedures include the use of a retractor for holding opening or securing patient tissue such that the surgeon can reach the tissue being treated. Retractors apply a force, such as a force vector, to the patient tissue to maintaining an opening. Because it may be difficult or undesirable to manually hold a position of a tool for such lengths of time, mechanical and/or electromechanical arms can be used to hold the position of the retractor while other aspects of the procedure are performed. Some arms can be adjustable such that a position of the arm, and the force applied by the retractor, can be adjusted before or during the procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Systems and methods for performing surgical retraction on patient anatomy using a surgical arm are described herein. In an example, the surgical arm can utilize a magnetorheological fluid power actuator within a surgical support arm to maintain a retraction force on an instrument affixed to the end of the surgical arm. The magnetorheological fluid powered surgical support arm can also include a force detection mechanism that supplies a control system with information about forces acting on the end of the surgical support arm. In response to detected forces, the surgical support arm, via the magnetorheological fluid powered actuator, can automatically reaction with counteracting or tracking movements to maintain a certain retraction force (e.g., maintain a pre-determined force vector relative to an external object).

Positionable, lockable surgical support arm systems can be used to hold surgical instruments in desired positions and orientations during a surgical procedure. However, a typical positionable surgical support arm cannot automatically move or track an external object. Additionally, typical surgical support arm systems are not adapted to maintain a desired retraction force even after movement of the retraction target. For example, if the patient moves during operation, the positionable surgical system may not necessarily adjust positioning of the surgical tool in response to that patient movement.

Magnetorheological fluid (MR fluid or MRF) is a type of smart fluid that can change properties in the presences of a magnetic field. For example, an MR fluid can greatly increase in apparent viscosity in the presence of a magnetic field. MR fluids can become viscoelastic solids in certain examples when subjected to a magnetic field. The viscosity of the fluid can be finely controlled by variations in the magnetic field intensity, which means the ability for the fluid to transmit force can be controlled through use of an electromagnet.

Use of MR fluid within a control system of a robotic arm or a simpler surgical support arm, can be adapted to enable a set retraction force to be maintained through movement of the retracted object.

As used herein, the terms "proximal" and "distal" should be given their generally understood anatomical interpretation. The term "proximal" refers to a direction generally toward the torso of a patient or base or handle of a tool, and "distal" refers to the opposite direction of proximal, such as away from the torso of a patient or toward the working end of the tool.

Figure 1:
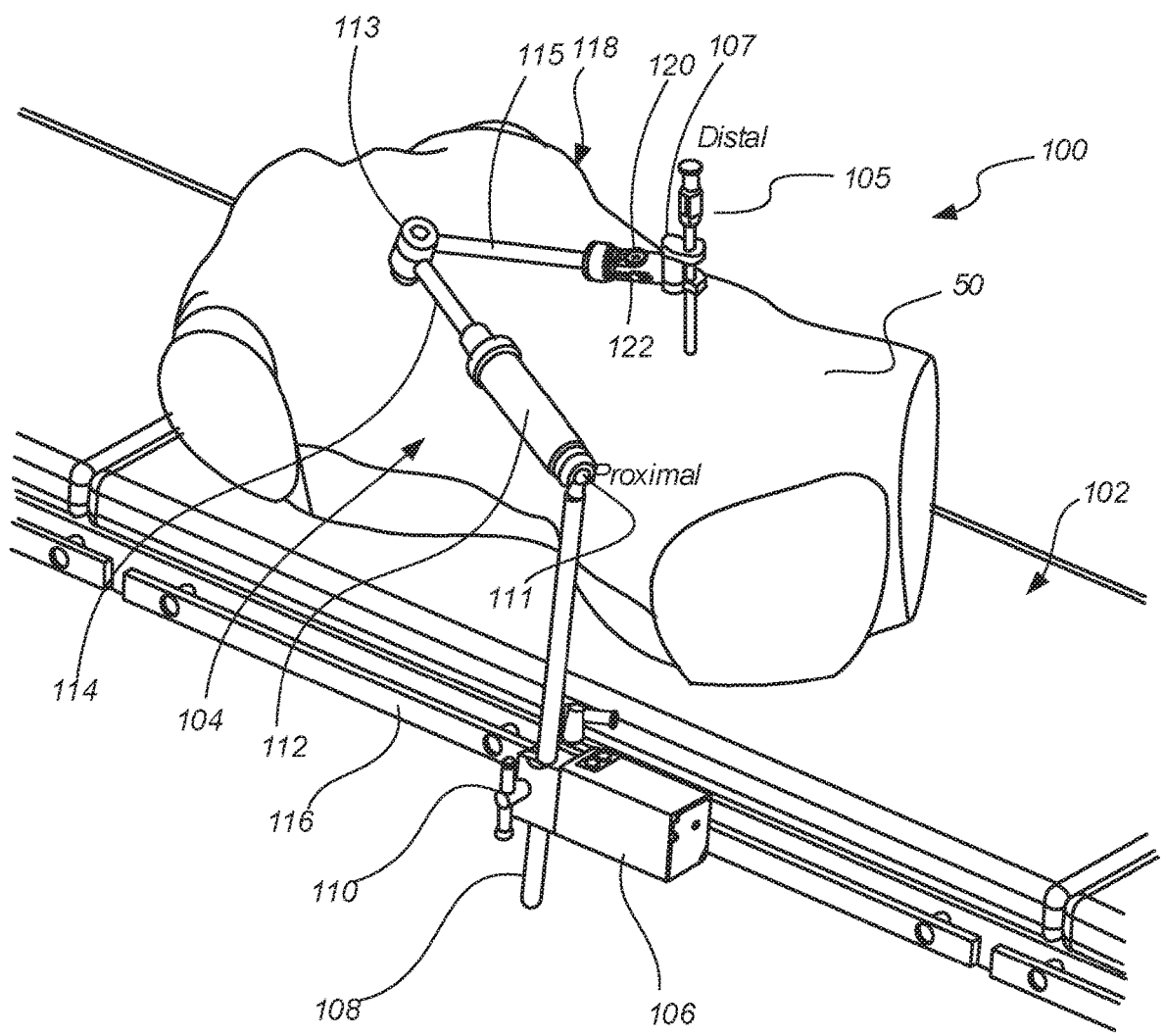
FIG. 1 illustrates a perspective view of a repositionable surgical arm system, in accordance with at least one example of this disclosure.

FIG. 1 illustrates a perspective view of repositionable, lockable surgical arm system 100, in accordance with at least one example of this disclosure. Lockable surgical arm system 100 can include table 102, arm 104, instrument 105, base unit 106, and instrument holder 107. Table 102 can include rail 116. Base unit 106 can include pole 108 and manual clamp 110. Arm 104 can include proximal joint 111, actuator unit 112, distal joint 113, proximal arm 114, distal arm 115, end effector coupler 118, lock/unlock button 120, and force sensor 123. Also shown in FIG. 1 are orientation indicators Proximal and Distal (shown and discussed with respect to the adjustable arm).

Base unit 106, which can include power control circuit components for an electrically powered actuator (such as actuator 112), can be secured to rail 116 of surgical table 102 using, for example, a clamp. Manual clamp 110a of base unit 106 can be operated to tighten base unit 106 against railing 116 and manual clamp 110b can be operated for adjustment of pole 108 to set a height of arm 104 above surgical table 102. Instrument holder 107 can be securable to a distal end of end effector coupler and can be configured to retain various instruments in a fixed (or adjustable) position relative to arm 104.

Electric actuator unit 112 of arm 104 can be located near a proximal end of arm 104 and can be coupled to pole 108 at proximal joint 111. Electric actuator 112 can also be coupled to a proximal portion of proximal arm 114. Proximal arm 114 can be coupled to electric actuator 112 via a joint or as an actuatable part of actuator 112 in other examples. Distal arm 115 can be coupled to a distal portion of proximal arm 114 via distal joint 113. Effector coupler 118 can connect instrument 105 to the distal end of arm 104. In some examples, lock/unlock button 120 can be provided on or near end effector coupler 118.

In some cases, instrument 105 can be a surgical retractor, such as for retraction of the knee, ribs, or other body parts. The retractor can be, for example, for separating the edges of a surgical incision or wound, to hold back underlying organs and tissues, or combinations thereof, so that body parts under the incision can be accessed by the surgeon. The retractor can, for example, have a curved, hooked, or angled blade with a handle, such that the retractor stays in place and maintains the desired position of the given region of tissue. The retractor can, for example, be clamped in placed or suspended from arm system 100.

The arms of lockable surgical arm system 100 can comprise a serial linkage of arm segments joined by spherical and/or rotational joints. Each of joints 111 and 113 (and any other joints in other examples) can be pivotable and/or rotational joints allowing movement of connected components with one or more degrees of freedom. Joints 111 and 113 (and joints within actuator 112) can be locked and unlocked using base unit 106 and actuator 112, which can be an electric bilateral actuator. In some examples, the joints of the arm can be locked and unlocked with a fluid, pneumatic, or hydraulic system.

In some cases, electric actuator unit 112 can be a magnetorheological (MR) fluid actuator, MR fluid is a type of smart fluid, and can be a series of magnetic particles suspended in a carrier oil. When an MR fluid is subjected to a magnetic field, it can increase in viscosity due to the alignment of the particles. The yield stress of an MR fluid can be meticulously controlled by varying magnetic field intensity.

For example, electric actuator unit 112 can be a power transmission including a gear motor, a MR fluid clutch, and a force transfer mechanism coupled to arm 104. In this case, electrical current supplied to the clutch can modify the magnetic field, which in turn can change the viscosity of the MR fluid. During slippage, an MR fluid clutch can, for example, decouple the dynamic behavior of the gear motors. This can, for example, mean the actuator has a high torque resolution and less non-linear effect such as backlash.

While only proximal arm 114 and distal arm 115 are shown in FIG. 1, additional arm segments can be provided between actuator 112 and end effector coupler 118 to comprise a serial linkage of arm segments, joined by spherical or rotational joints. Each additional arm segment may require one or more additional joints to form a repositionable, lockable support arm structure. Such additional arm segments can provide greater coverage and ability for the arm to be positioned with more degrees of freedom in the surgical field.

In operation of some examples, lock/unlock button 120 can be operable by a user to initiate power locking and unlocking of arm 104. When lock/unlock button 120 is not depressed arm 104 can be in a locked state where joints 111 and 113 are locked such that proximal arm 114 and distal arm 115 cannot move relative to each other or to table 102. When lock/unlock button 120 is pressed, actuator 112 can unlock joints 111 and 113 such that end effector coupler 118 can be positioned, as desired, and as guided by joints 111 and 113 and proximal arm 114 and distal arm 115. That is, end effector coupler 118 can be moved to a desired position relative to body 50 through movement paths limited by the freedom of arm 104 to position instrument 105 to a desired position relative to body 50.

In some case, arm system 100 can further include a force sensor 123. Force sensor 123 can be, for example, positioned near the distal end of distal arm 115, integrated with or adjacent to end effect coupled 118. Force sensor 123 can be, for example, aligned such that force sensor 123 can detect changes in force applied to the body 50 by instrument 105. Changes in force can include, for example, movement in the body 50, movement of the surgeon, or other movement.

Force sensor 123 can be, for example, a thin-film force sensor, a force-sensitive resistor, a torque transducer, or other type of sensor as appropriate. Forces sensor 123 can, in some cases, including MR fluid in the sensor to allow for more precise detection of changes in force the instrument 105 applies to the body 50. The use of MR, fluid in force sensor 123 can, for example, allow for precise detection of changes in force applied by instrument 105.

With the use of force sensor 123 and MR actuator 112, system 100 can move and articulate instrument 205 based on force alone, without additional optical sensing.

FIG. 2A illustrates a perspective view of surgical arm system 200, in accordance with at least one example of this disclosure. FIG. 2B illustrates a perspective view of surgical arm 200, in accordance with at least one example of this disclosure. FIGS. 2A and 2B are discussed below concurrently.

Figure 2:
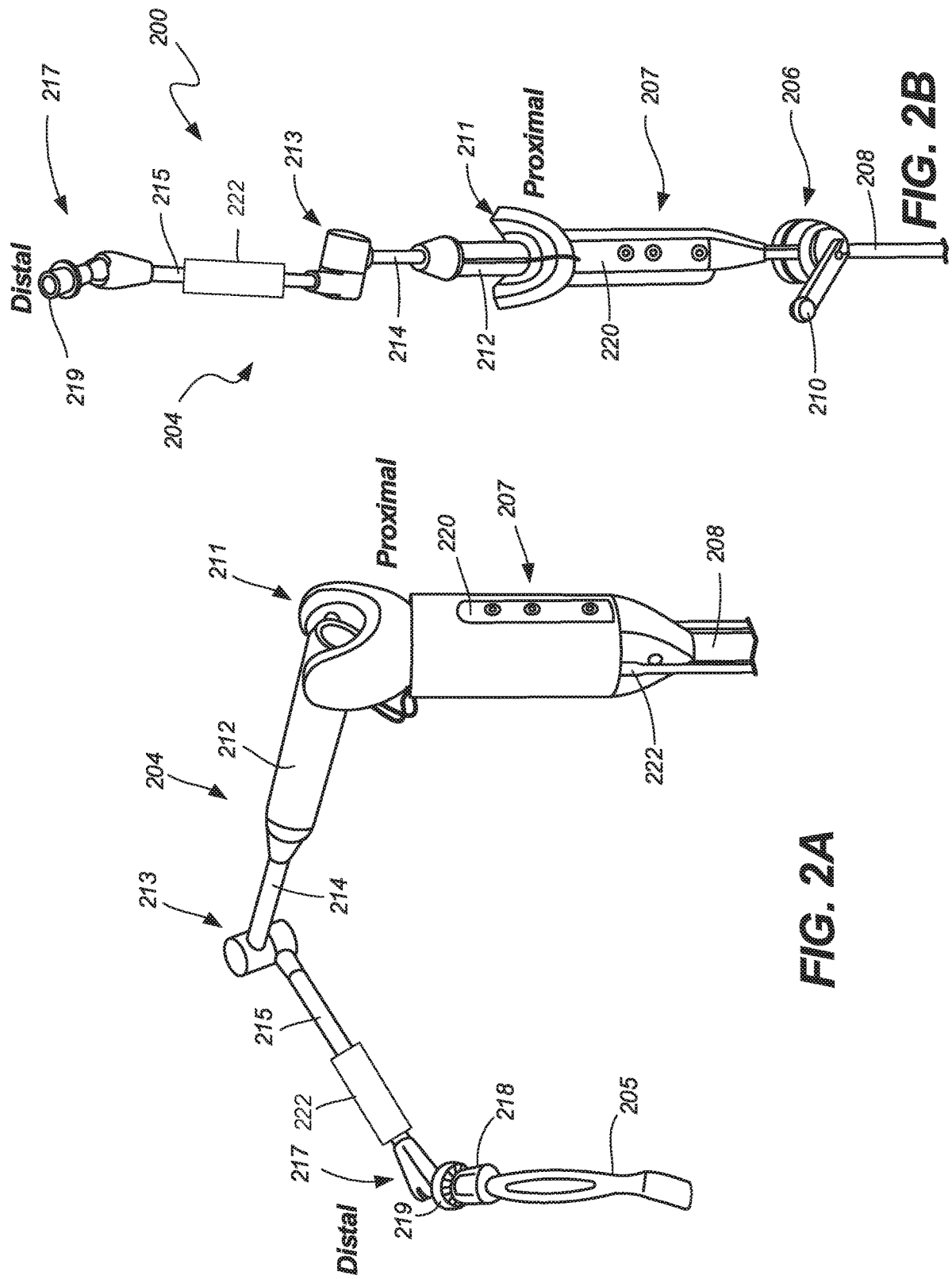
FIG. 2A illustrates a perspective view of a repositionable surgical arm, in accordance with at least one example of this disclosure.
FIG. 2B illustrates a perspective view of a repositionable surgical arm, in accordance with at least one example of this disclosure.

Surgical arm system 200 can include arm 204, instrument 205, control device 207, pole 208, and manual clamp 210. Arm 204 can include proximal joint 211, actuator unit 212, distal joint 213, proximal arm 214, distal arm 215, coupler joint 217, end effector coupler 218, arm coupler 219, and force sensor 223. Control device 207 can include user interface 220 and can be connected to cable 222. Also shown in FIG. 2 are orientation indicators Proximal and Distal.

Surgical arm system 200 can be similar to system 100 discussed above, except that surgical arm 200 can include different features.

In arm 204, arms 214, 215, and couplers 218, 219, are connected by joints 211, 213, 217. Actuator unit 212 can reside on or near distal arm 215. Force sensor 223 can reside on or near proximal arm 214. In arm 204, a base unit can be a manually adjustable unit, where manual clamp 210 can be operable to adjust a position of base unit 206 along a rail (e.g., surgical table rail) and to adjust the height of pole 208 (and therefore arm 204).

Instrument 205 can be held on or near end effect coupler 218 and arm coupled 219. Instrument 205 can be, for example, a surgical instrument for applying force or tension to target body tissue. For example, instrument 205 can be a retractor as described with reference to FIG. 1 about.

In surgical arm system 200, control device 207 can include electronic components configured to control arm 204. For example, control device 207 can house a controller (discussed further below) and user interface 220, which can include one or more control inputs (such as buttons and switches) and can include audible or visual indicia. Cable 222 can be couple-able to control device 207 to connect a lock/unlock button to control device 207. Actuator unit 212 can be coupled to control device 207 and arm 204. Actuator unit 212 can be used to engage arm 204 to apply a given amount of force using instrument 205. Actuator unit 212 can be, for example, an MR fluid-based actuator, such as an MR power transmission as discussed with reference to FIG. 1.

Force sensor 223 can be coupled to control device 207 and arm 204. Force sensor 223 can be used to monitor and detect changes in forces applied to instrument 205 on the target tissue. For example, force sensor 223 could detect changes in forces due to patient movement. Force sensor 223 can allow for feedback to surgical arm system 200 so that surgical arm system 200 does not need to rely on optical sensing for the positioning of instrument 205.

Control device 207 can allow for alteration of the force being applied through instrument 205 based on information received from force sensor 223, as discussed in more detail below.

Figure 3:
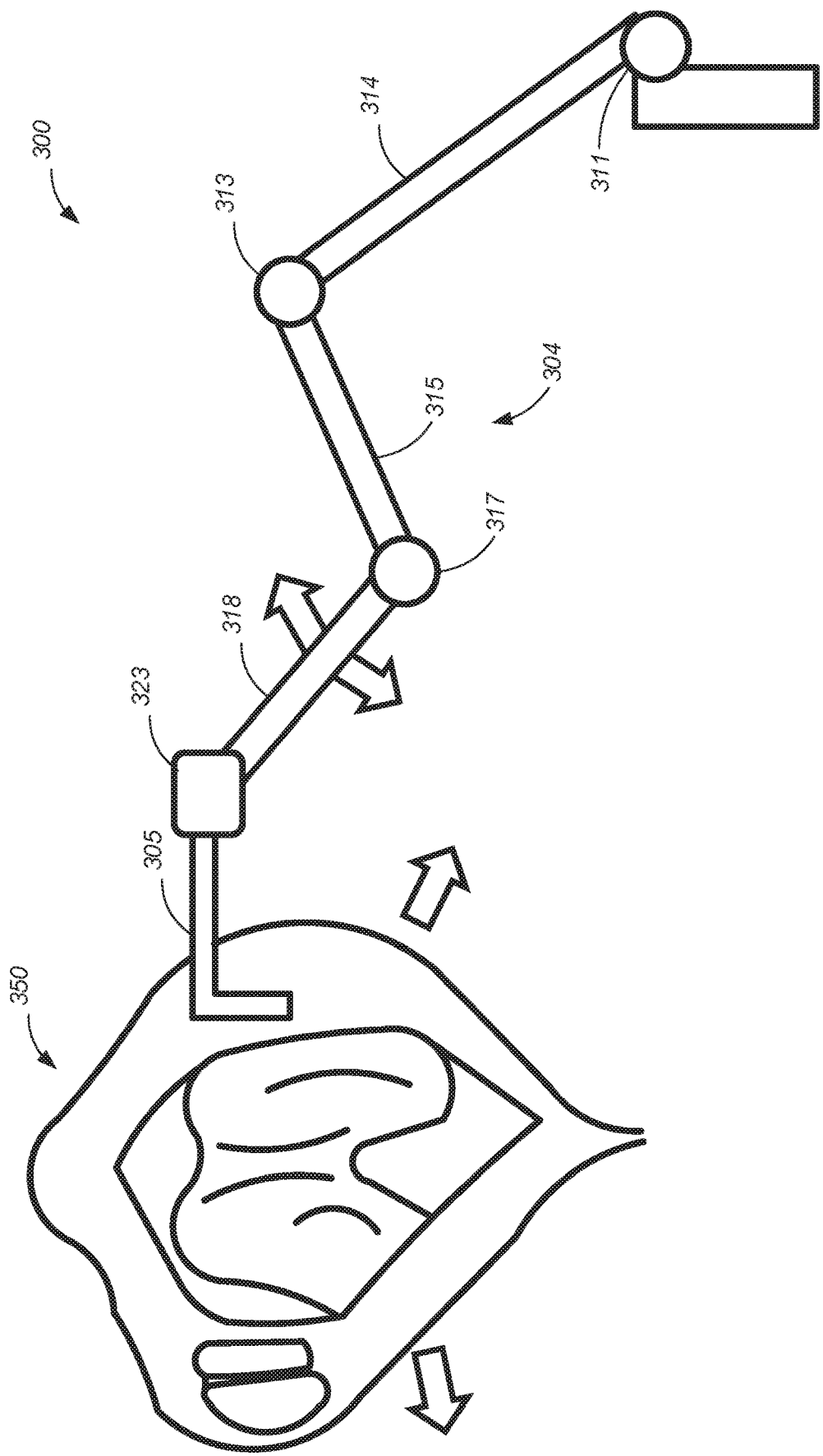
FIG. 3 illustrates a diagram of a surgical arm for retraction in accordance with some embodiments.

FIG. 3 illustrates a diagram of a surgical arm system 300 for retraction in accordance with some embodiments. The surgical arm system 300 includes a force or torque sensor 323, a retractor 305, and an arm component 304. Surgical arm system 300 can have a proximal end and distal end. Surgical arm system 300 can be coupled to a controller such as described with reference to FIGS. 1, 2A-2B, above.

In some examples, the surgical arm system 300 can include a robotic arm (e.g., include power driven joints and associated controller). The arm component 304 may include any of the configurations described above with respect to FIGS. 1 and 2A-2B, for example. In one example, arm component 304 can include an MR actuator unit 311, distal joint 313, proximal arm 314, distal arm 215, coupled joint 317, end effector coupler 318, and arm coupler 319, connected as described in reference to FIG. 1 above.

Retractor 305 can be, for example, a surgical retractor, such as for retraction of the knee, ribs, or other body parts. Retractor 305 can be, for example, for separating the edges of a surgical incision or wound, to hold back underlying organs and tissues, or combinations thereof, so that body parts under the incision can be accessed by the surgeon. Retractor 305 can, for example, have a curved, hooked, or angled blade with a handle, such that retractor 305 stays in place and maintains the desired position of the given region of tissue. Retractor 305 can, for example, be clamped in placed or suspended from surgical arm system 300.

Retractor 305 can be used to apply a constant force on the target tissue, such as, for example, about 5 N to about 6 N.

The force or torque sensor 323 may be located between the retractor and a distal portion 315 of the arm component. In some examples, the indicated force sensor 323 can be multiple sensors to received data from different vectors or orthogonal directions. Additionally, another force or torque sensor 323 may be located between two portions of the arm component.

In an example, the surgical arm 304 may be moved by a magnetorheological fluid force application component, such as MR actuator 311, which may be located at a proximal portion of the surgical arm 304. In an example, the MR actuator 311 may include components throughout the surgical arm 304, such as a motor, locks, MR fluid force application components, or the like. The magnetorheological fluid force application component may apply a force, such as at a base (e.g., from where the surgical arm is fixed to a bed supporting the patient) to the surgical arm. For example, the magnetorheological fluid force application component may cause the retractor 305 to apply a force to patient anatomy. In an example, the joints 313, 317, or the like, may be locked during a surgical procedure, such that surgical arm 304 acts as a rigid body, and a force maintained or changed by the MR actuator 311 acts on the retractor 305 via the rigid body of the surgical arm 304. The joints may be adjusted for convenience. In another example, the MR actuator 311 is in joint 317 (e.g., a distal joint) and causes the retractor 305 to move via movement of the end effector coupler 318, which may be a rigid portion of the surgical arm 304 (e.g., an arm between the force sensor 323 and the distal joint 317). In this example, remaining joints of the surgical arm 304 may be locked to prevent movement of the proximal arm 314 and the distal arm 315, for example.

The force applied by the retractor 305 may be a constant force, such that when the patient moves, the force is maintained. The force can be, for example, about 5 N. The force may be maintained by receiving feedback at a controller from the force or torque sensor. The controller may use the feedback force to control the output of force by the magnetorheological fluid force application component. In another example, a force application component may use other force applying techniques, such as electromechanical, mechanical, hydraulic, or the like.

Maintaining a constant force by the retractor 305 on the patient anatomy 350 may be done without tracking of the surgical arm 304 or the patient. For example, the only feedback used by the surgical arm to maintain the constant force may be the feedback received from the force or torque sensor 323, The controller can utilize changes in the detected force to move the retractor 305, via surgical arm 304, to maintain the desired retraction force. The retractor 305, via the surgical arm 304, can be positioned and a force vector applied to implement the desired retraction, such as tissue retraction at a surgical site. Through feedback received from the force and/or torque sensor(s) 323, the surgical arm 304 can automatically react to maintain the set force vector with respect to the retraction target.

Figure 4:
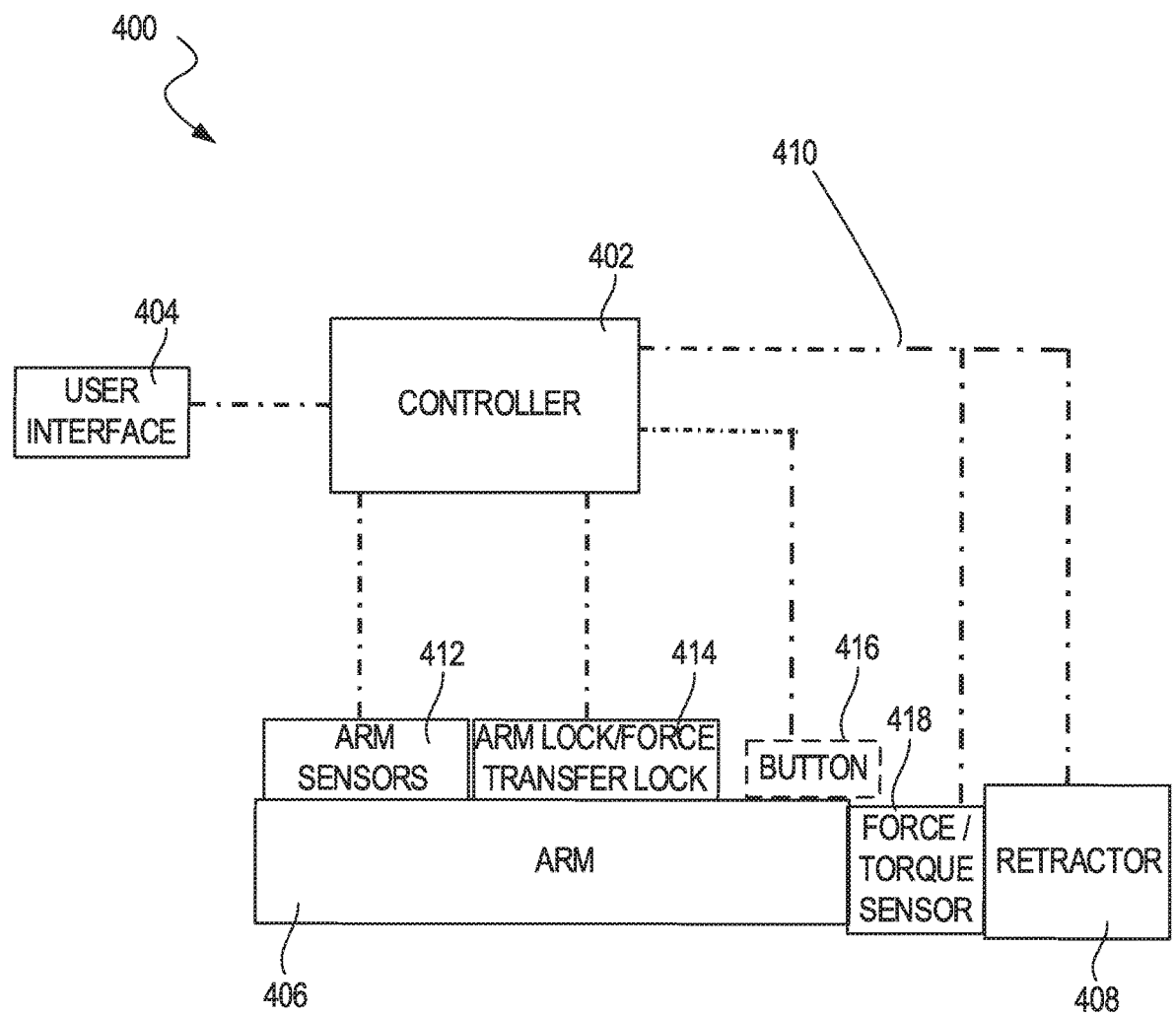
FIGS. 4-5 illustrate retractor systems in accordance with some embodiments.
Figure 5:
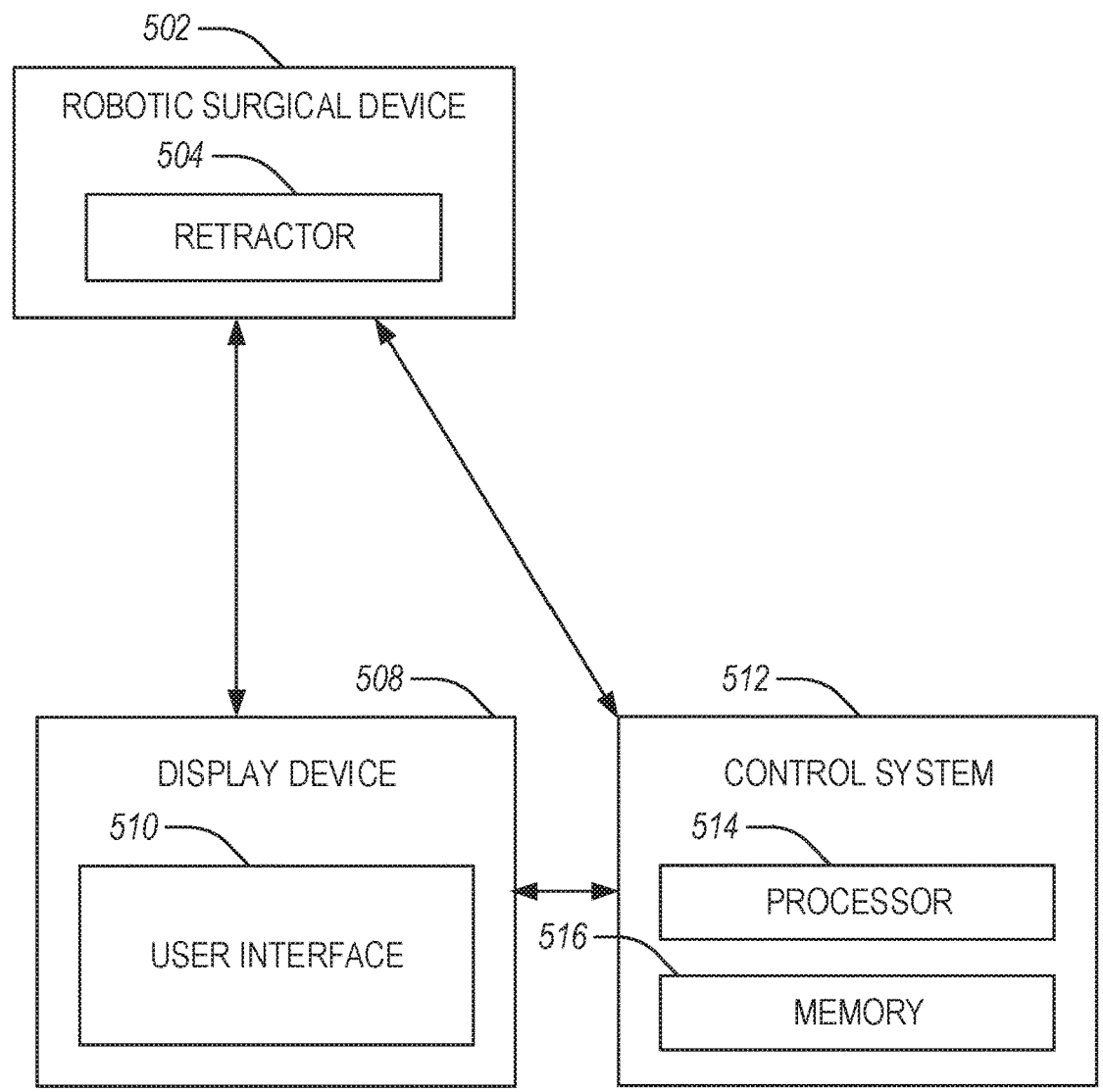

FIGS. 4-5 illustrate retractor systems in accordance with some embodiments.

FIG. 4 is a block diagram of a retractor system including a surgical support arm, in accordance with some embodiments. The retractor system 400 can include a controller 402, a user interface 404, a surgical support arm 406, a retractor 408, communication channels 410, arm sensors 412, and arm lock/force transfer lock 414. In some examples, the surgical support arm 406 can include a button 416 for user activation and force and/or torque sensors 418 disposed between the surgical support arm 406 and the retractor 408.

Controller 402 can, for example, be in communication with, collect data from, and/or direct actions of, arm sensors 412, arm lock/force transfer lock 414, force sensor 418, and retractor 408 through communication channels 410. For example, force sensor 418 can detected a chance in force on retractor 408. The sensed force can be transmitted to controller 402, which can in turn, alter arm 406 based on this information. In some cases, a user can manually input information to controller 402 through user interface 404.

Surgical support arm 406 can be articulated through controller 402 via arm sensors 412 and arm lock/force transfer lock 414, or manually by the user through button 414. Surgical support arm 406 can hold and articulate retractor 408 as directed.

Arm sensors 412 can include one or more sensors on or near arm 406, situated to help position arm 406 when activated. Arm sensors 412 can be, for example, optical sensors used to visually situate arm 406 when in use. In some cases, arm sensors 412 can be force or torque sensors situated on arm 412 to detect specific changes in force, such as force sensor 418.

Arm lock/force transfer lock 414 can be a mechanism for locking arm 406 in a particular position and force vector. Arm lock/force transfer lock 414 can be positioned to allow the desired amount of force to be director by retractor 408. For example, arm lock/force transfer lock 414 can induce retractor 408 to apply a desired force vector or a specific force lock value depending on the surgery being performed.

Retractor 408 can apply force to target tissue so as to allow for surgery in an incision, Retractor 408 can, for example, apply a constant force on the tissue to maintain a steady opening. Force sensor 418 can be, for example, a force or torque sensor for detecting a change in force directed to the target tissue by retractor 408. In some cases, force sensor 418 can contain MR fluid. In system 400, controller 402 can direct movement and action of surgical support arm 406 holding instrument 405. For example, the operator can secure retractor 408 to surgical support arm 406. The operator can then direct the surgical support arm, through user interface 404 and controller 402, to apply the retractor 408 to the patient's knee or other tissue needing retracting. The operator can determine the appropriate force, such as a force vector, to be applied to the knee. For example, this can be a force vector of about 5 N to about 6 N in a knee retraction surgery. The operator can manipulate the direction of the force vector using user interface 404 and controller 402 so that the force is applied in the correct direction to hold the knee open. The force may be maintained at a constant force (or within a constant range of forces) to retract, for example, soft tissue of a knee during an arthroplasty.

The operator can then continue on to the surgical procedure to be done inside the knee (or other tissue) held open by the retractor. Throughout the procedure, force sensor 418 can monitor the force vector applied by retractor 405 onto the knee. If the force vector is altered, the force sensor 418 can indicate the change in force or change in the force vector to the controller 402 by sending a sensed change in force along pathway 410. The force sensor 418 can be, for example, a highly sensitive MR fluid-type force sensor or torque sensor, containing an MR fluid that is altered based on magnetic fields. This can allow for very slight changes in force to be detected.

In response, the controller 402 can alter the amount or direction of force on the knee by the retractor 405. The controller 402 can do this by changing the action of the actuator integrated with the surgical support arm 406. Examples of an actuator are discussed above with reference to FIGS. 1-3. The actuator can, for example, be an MR fluid type actuator.

Throughout the surgical procedure, the force sensor 418 can monitor the force vector applied to the knee so that controller 402 can direct appropriate changes in force during the surgical procedure. This can result in an overall constant force vector applied by the retractor 405 to the knee, regardless of outside movement or external forces.

FIG. 5 is a block diagram illustrating components of a robotic surgical device, in accordance with some embodiments. In this example, the robotic system 500 can include a robotic surgical device 502, a retractor 504, a display device 508, a user interface 510, and a control system 512. The control system 512 can include a processor 514 and memory 516.

Robotic surgical device 502 can be, for example, device 100, 200, or 300, discussed above, including a retractor 504 for holding patient tissue in place. The robotic surgical device 502 can be coupled to the display device 508, user interface 510, and control system 512.

Display device 508 can show information related to system 500, such as timing, force being applied to retractor 504, the chosen program, the chosen force vector or force lock, or other information. User interface 510 can be, for example, a touch screen, buttons, keys, or other way for a user to interact with the robotic system 500, such as to input changes to the program.

Control system 512 can include a processor 514 and memory 516. Control system 512 can, for example, function similarly to the controller described with reference to FIG. 4 above. Control system 512 can manipulate the position of robotic surgical device 502, for example, based on sensed force data from an NM based sensor.

Figure 6:
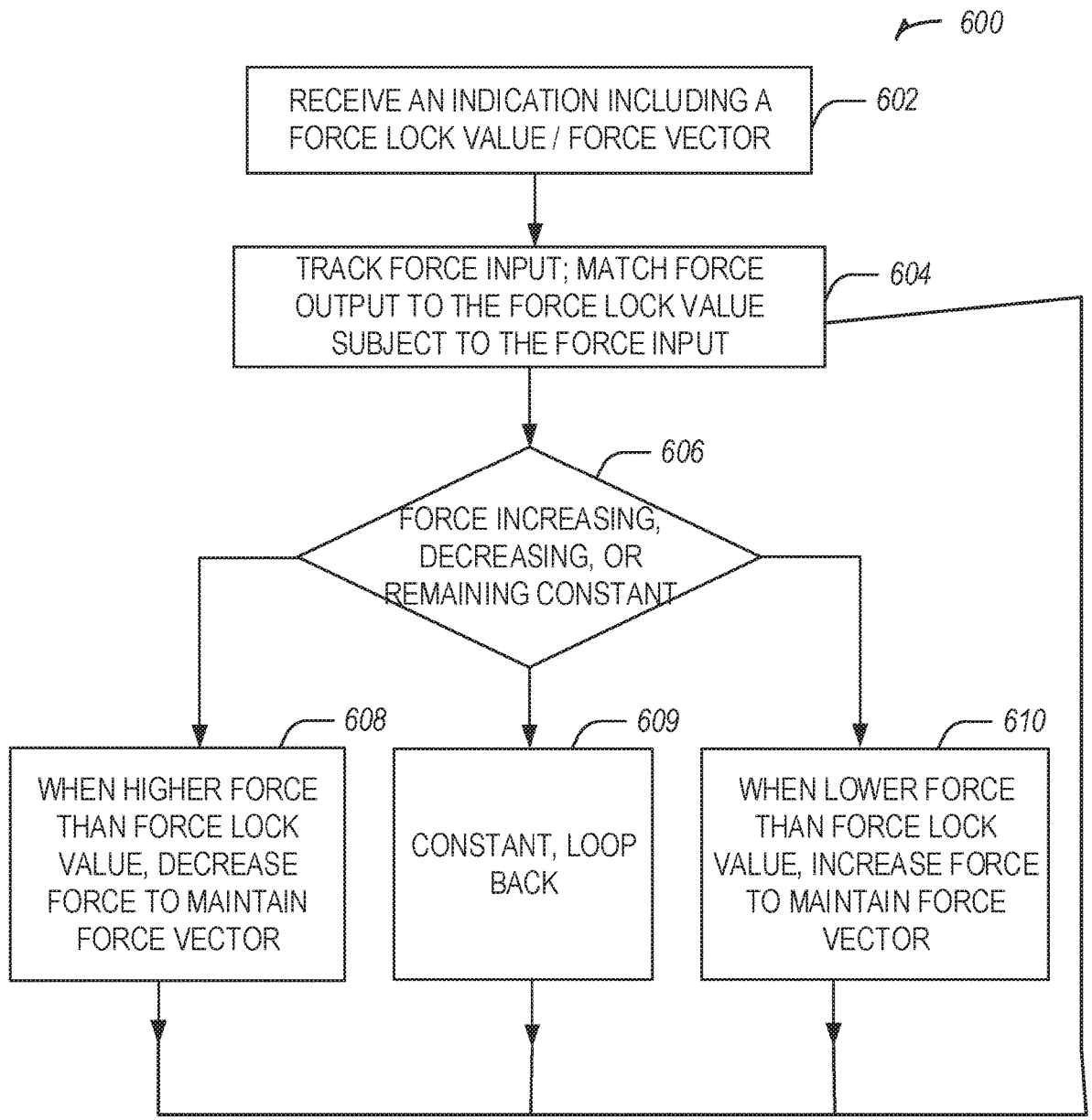
FIG. 6 illustrates a flowchart showing a technique for maintaining a constant retraction force using a surgical arm in accordance with some embodiments.

FIG. 6 illustrates a flowchart illustrating a technique 600 for maintaining a constant retraction force using a surgical arm in accordance with some embodiments.

The technique 600 includes an operation 602 to receive an indication including a force lock value (a constant force to be maintained) or a force vector (including direction), such as at a user interface, via a hardware button or component, or in a collaborative mode (e.g., a surgeon retracts patient tissue collaboratively, such as using a force-assist from the surgical arm) In an example, a surgeon can retract patient tissue while activating a force vector button on the surgical arm.

The technique 600 includes an operation 604 to track force input (e.g., applied on the surgical arm, such as by the patient anatomy when the patient moves), and match force output to the force lock value or the force vector or the set force attributes, subject to the force input.

The technique 600 includes a decision operation 606 to determine whether the force applied on the surgical arm is increasing, decreasing, or remaining constant. Upon release of the force vector button, the surgical support arm can engage a mode to maintain a force vector recorded upon release of the force vector button. In an example, sensors on the surgical support arm can detect the force vector, and that information can be utilized by a controller to maintain the detected force vector.

The technique 600 includes operations 608-610 to modify the force applied by the surgical arm in response to the force applied on the surgical arm to maintain a constant force on the patient anatomy. As indicated by the operations, a controller within the surgical support arm can received force information from sensors and react accordingly to maintain the set force vector.

Figure 7:
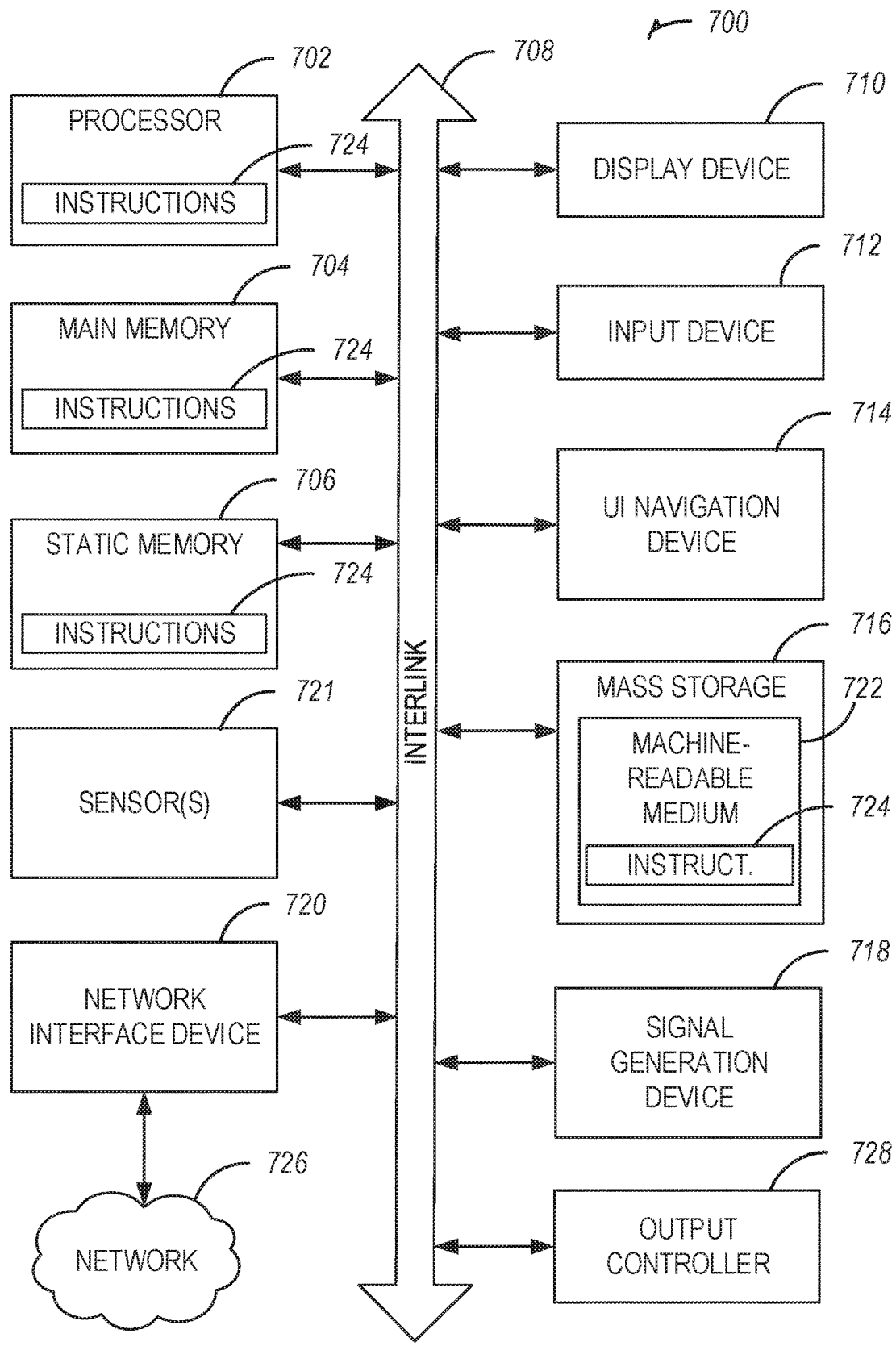
FIG. 7 illustrates a block diagram of an example machine upon which any one or more of the techniques discussed herein may perform in accordance with some embodiments.

FIG. 7 illustrates a block diagram of an example machine 700 upon which any one or more of the techniques discussed herein may perform in accordance with some embodiments. In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710, an alphanumeric input device 712. (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724. The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MEMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Each of these non-limiting examples may stand on its own, or may be combined in various permutations or combinations with one or more of the other examples.

Example 1 can include system comprising: a surgical arm having a distal end opposite a proximal end; a retractor, connected to the surgical arm on or near the distal end, configured to apply a force to a portion of patient anatomy; a force sensor mounted on the surgical arm between the retractor and the proximal end, the force sensor configured to output a voltage indicating force on the retractor via movement of the portion of patient anatomy; and a magnetorheological fluid actuator for actuating the surgical arm, the actuator configured to adjust the surgical arm according to the received voltage to cause the retractor to maintain a constant retraction force on the portion of patient anatomy.

Example 2 can include Example 1, wherein the magnetorheological fluid actuator comprises a power transmission.

Example 3 can include any of Examples 1-2, wherein the power transmission comprises a gear motor and one or more magnetorheological clutches.

Example 4 can include any of Examples 1-3, wherein the portion of patient anatomy includes soft tissue of a knee.

Example 5 can include any of Examples 1-4, wherein the force sensor comprises a torque sensor.

Example 6 can include any of Examples 1-5, wherein the force sensor comprises a thin-film force sensor.

Example 7 can include any of Examples 1-6, wherein the constant retraction force comprises about 5 N to about 6 N.

Example 8 can include any of Examples 1-7, further comprising a base for mounting the surgical arm.

Example 9 can include any of Examples 1-8, further comprising a control device in communication with the surgical arm and operable to transmit a signal to alter the amount of force applied by the retractor.

Example 10 can include a method for retracting tissue comprising: receiving a retraction force value; applying force to the tissue using a magnetorheological fluid actuator to induce the retraction force; sensing a change in force applied to the tissue using a force sensor; and maintaining the retraction force by adjusting the force applied to the tissue using the magnetorheological fluid actuator, based on the change in force.

Example 11 can include Example 10, wherein the retraction force value comprises a force lock value.

Example 12 can include any of Examples 10-11, wherein the retraction force value comprises or a force vector.

Example 13 can include any of Examples 10-12, wherein the change in force comprises patient movement causing the tissue to move.

Example 14 can include any of Examples 10-13, wherein the change in force comprises operator movement.

Example 15 can include any of Examples 10-14, wherein the force sensor comprises a torque sensor.

Example 16 can include any of Examples 10-15, wherein the retraction force value comprises about 5 N to about 6 N.

Example 17 can include at least one non-transitory machine-readable medium including instructions, which when executed by a processor of a machine, cause the processor to perform operations comprising: receiving a retraction force value; applying force to the tissue using a magnetorheological fluid actuator to induce the retraction force; sensing a change in force applied to the tissue using a force sensor; and maintaining the retraction force by adjusting the force applied to the tissue using the magnetorheological fluid actuator, based on the change in force.

Example 18 can include Example 17, wherein the retraction force value comprises a force lock value.

Example 19 can include any of Examples 17-18, wherein the retraction force value comprises a force vector.

Example 20 can include any of Examples 17-19, wherein the change in force comprise patient movement causing the tissue to move.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A system comprising:
   a surgical arm having a distal end opposite a proximal end;
   a retractor, connected to the surgical arm on or near the distal end, configured to apply a force to a portion of patient anatomy;
   a force sensor mounted on the surgical arm between the retractor and the proximal end, the force sensor configured to output a voltage indicating force on the retractor via movement of the portion of patient anatomy; and
   a magnetorheological fluid actuator for actuating the surgical arm, the actuator configured to adjust the surgical arm according to the received voltage to cause the retractor to maintain a constant retraction force on the portion of patient anatomy; and
   a control device in communication with the surgical arm and operable to transmit a signal to alter the amount of force applied by the retractor.

2. The system of claim 1, wherein the magnetorheological fluid actuator comprises a power transmission.

3. The system of claim 2, wherein the power transmission comprises a gear motor and one or more magnetorheological clutches.

4. The system of claim 1, wherein the portion of patient anatomy includes soft tissue of a knee.

5. The system of claim 1, wherein the force sensor comprises a torque sensor.

6. The system of claim 1, wherein the force sensor comprises a thin-film force sensor.

7. The system of claim 1, wherein the constant retraction force comprises 5 N to 6 N.

8. The system of claim 1, further comprising a base for mounting the surgical arm.

\* \* \* \* \*